(12) United States Patent
Chen

(10) Patent No.: US 10,000,395 B2
(45) Date of Patent: Jun. 19, 2018

(54) HIGH-MAGNESIUM CONCENTRATED LIQUID AND HIGH-MAGNESIUM POTABLE-WATER MIXING SYSTEM

(71) Applicant: QUALITY PURE CO., LTD., Taipei (TW)

(72) Inventor: Guan-Hao Chen, Taipei (TW)

(73) Assignee: QUALITY PURE CO., LTD., Taipei (TW)

( * ) Notice: Subject to any disclaimer, the term of this patent is extended or adjusted under 35 U.S.C. 154(b) by 0 days. days.

(21) Appl. No.: 15/277,148

(22) Filed: Sep. 27, 2016

(65) Prior Publication Data

US 2018/0057376 A1    Mar. 1, 2018

(30) Foreign Application Priority Data

Aug. 26, 2016   (TW) .............................. 105127429 A

(51) Int. Cl.
| | |
|---|---|
| C02F 1/44 | (2006.01) |
| C02F 9/00 | (2006.01) |
| B01D 61/14 | (2006.01) |
| A61K 9/08 | (2006.01) |
| A23L 2/00 | (2006.01) |

(Continued)

(52) U.S. Cl.
CPC .............. *C02F 1/686* (2013.01); *A61K 9/08* (2013.01); *A61K 33/00* (2013.01); *A61K 33/06* (2013.01); *B01D 61/022* (2013.01); *C02F 1/005* (2013.01); *C02F 1/441* (2013.01); *C02F 9/00* (2013.01)

(58) Field of Classification Search
CPC ...... B01D 9/00; B01D 9/0018; B01D 9/0031; B01D 9/0059; B01D 61/04; B01D 61/10; B01D 61/14; B01D 61/142; B01D 61/145; B01D 61/147; B01D 61/16; B01D 61/20; B01D 61/58; B01D 2311/02; B01D 2311/04; B01D 2311/2673; B01D 61/02; B01D 61/022; C02F 1/005; C02F 1/686; C02F 1/04; C02F 1/44; C02F 1/441; C02F 1/444; C02F 9/00; C02F 2103/08; C02F 1/02; A61K 9/08; A61K 33/06; A61K 33/10; A23L 2/00; A23L 2/74

USPC ... 210/96.2, 101, 182, 257.2, 258, 259, 641, 210/652, 790, 806; 426/66, 74; 423/580.1

See application file for complete search history.

(56) References Cited

U.S. PATENT DOCUMENTS

| | | | |
|---|---|---|---|
| 4,141,825 A * | 2/1979 | Conger | B01D 61/58 210/638 |
| 4,161,446 A * | 7/1979 | Coillet | B01D 61/025 210/181 |

(Continued)

FOREIGN PATENT DOCUMENTS

EP    2298702 B1    1/2014

*Primary Examiner* — Joseph Drodge

(74) *Attorney, Agent, or Firm* — Muncy, Geissler, Olds & Lowe, P.C.

(57) ABSTRACT

A high-magnesium concentrated liquid is disclosed. In a first embodiment, the high-magnesium concentrated liquid comprises magnesium ranged from 60000-70000 ppm, sodium ranged from 1000-3200 ppm, potassium ranged from 300-3000 ppm, calcium ranged from 100-300 ppm, and the balance of water. In a second embodiment, the high-magnesium concentrated liquid comprises magnesium ranged from 40000-50000 ppm, sodium ranged from 8000-18000 ppm, potassium ranged from 8000-17000 ppm, calcium ranged from 15-250 ppm, and the balance of water.

10 Claims, 12 Drawing Sheets

(51) Int. Cl.
  *B01D 61/02* (2006.01)
  *C02F 1/68* (2006.01)
  *A61K 33/06* (2006.01)
  *A61K 33/00* (2006.01)
  *C02F 1/00* (2006.01)

(56) References Cited

U.S. PATENT DOCUMENTS

| | | | | |
|---|---|---|---|---|
| 4,169,789 A | * | 10/1979 | Lerat | B01D 61/025 210/257.2 |
| 4,434,057 A | * | 2/1984 | Marquardt | B01D 61/025 203/39 |
| 5,814,224 A | * | 9/1998 | Khamizov | B01J 39/02 210/638 |
| 7,329,358 B2 | | 2/2008 | Wilkins et al. | |
| 2002/0166758 A1 | * | 11/2002 | Vinz | B01D 1/26 203/2 |
| 2006/0144789 A1 | * | 7/2006 | Cath | B01D 61/002 210/641 |
| 2008/0292755 A1 | * | 11/2008 | Green | A23L 2/52 426/66 |
| 2010/0163471 A1 | * | 7/2010 | Elyanow | B01D 61/022 210/176 |
| 2011/0198285 A1 | * | 8/2011 | Wallace | C01B 7/03 210/638 |
| 2011/0303606 A1 | * | 12/2011 | Takeuchi | B01D 61/58 210/638 |
| 2012/0160753 A1 | * | 6/2012 | Vora | B01D 61/022 210/175 |
| 2012/0305459 A1 | * | 12/2012 | Takabatake | B01D 61/022 210/97 |
| 2012/0328738 A1 | * | 12/2012 | Green | A23L 33/16 426/66 |
| 2013/0002001 A1 | * | 1/2013 | Allen | B64D 11/06 297/411.3 |
| 2013/0056417 A1 | * | 3/2013 | Abd Ellatif | C02F 1/442 210/639 |
| 2014/0151300 A1 | * | 6/2014 | Savage | C02F 9/00 210/638 |
| 2014/0197029 A1 | * | 7/2014 | Sparrow | B01D 65/02 204/519 |
| 2014/0311980 A1 | * | 10/2014 | Weston | B01D 61/022 210/652 |
| 2015/0376033 A1 | * | 12/2015 | Tao | C02F 1/44 210/639 |
| 2016/0244648 A1 | * | 8/2016 | Adams | A23K 50/48 |

* cited by examiner

HIGH-MAGNESIUM CONCENTRATED LIQUID AND HIGH-MAGNESIUM POTABLE-WATER MIXING SYSTEM

FIELD OF THE INVENTION

The present invention relates to a potable-water concentrated liquid and a potable-water mixing system, particularly to a high-magnesium concentrated liquid and a high-magnesium potable-water mixing system.

BACKGROUND OF THE INVENTION

Water is an important constituent of human bodies. Appropriate supplement of water can improve metabolism and blood circulation of human bodies. Awakening to importance of healthcare, people have begun to demand the quality of potable water recently. Thus, the industry is also driven to develop the related technology.

A Europe patent No. 2298702B1 disclosed a potable-water purification device, which comprises a water purification chamber and a biocide dispensing box. The biocide dispensing box is in fluid communication with a biocide storage compartment and a biocide dispensing port. The water purification chamber is in fluid communication with a pure water discharge chamber through a filter. The pure water discharge chamber includes a water discharge mechanism. The prior art is characterized in that the water purification chamber includes a fill cup and that the fill cup includes an inlet port and a porthole. The fill cup is positioned at the top end of the water purification chamber and in fluid communication with the water purification chamber through the porthole. The device further comprises a vertical tube connected with the fill cup and the biocide dispensing box. A positive air pressure is created in the vertical tube connected with the biocide dispensing box to enable the biocide to be dispensed into the water purification chamber. A U.S. Pat. No. 7,329,358B2 disclosed a water purification method, which comprises steps: providing feed water into an electrochemical purification device; controlling hardness of the water from the electrochemical purification device to a hardness level in a range of 5 ppm-100 ppm as $CaCO_3$; controlling alkalinity of the water from the electrochemical purification device to an alkalinity level in a range of 10 ppm-100 ppm as $CaCO_3$; and supplying the water of controlled alkalinity and reduced hardness as purified water for human consumption.

The conventional technologies usually lay stress on removing the harmful materials in water. However, the conventional technologies do not pay attention to increasing the useful constituents of water. Therefore, the conventional technologies still have room to improve.

SUMMARY OF THE INVENTION

The primary objective of the present invention is to solve the problem that the potable water provided by the conventional technologies does not contribute positive effects to human bodies.

In order to achieve the abovementioned objective, the present invention provide a high-Mg concentrated liquid, which comprises magnesium ranged from 60000-70000 ppm, sodium ranged from 1000-3200 ppm, potassium ranged from 300-3000 ppm, calcium ranged from 100-300 ppm, and the balance of water.

In order to achieve the abovementioned objective, the present invention also provides another high-magnesium concentrated liquid, which comprises magnesium ranged from 40000-50000 ppm, sodium ranged from 8000-18000 ppm, potassium ranged from 8000-17000 ppm, calcium ranged from 15-250 ppm, and the balance of water.

In order to achieve the abovementioned objective, the present invention further provides a high-magnesium potable-water mixing system, which comprises a high-magnesium concentrated liquid output device providing the abovementioned high-magnesium concentrated liquid;

a purified water output device providing purified water; and a liquid mixing device interconnecting with the high-magnesium concentrated liquid output device and the purified water output device and mixing the high-magnesium concentrated liquid and the purified water to generate a high-magnesium potable water.

From the above description, it is learned: the present invention has an advantage over the conventional technologies: the high-magnesium concentrated liquid is experimentally proved to be useful in improving osteoporosis and relieve fatigue.

DETAILED DESCRIPTION OF THE PREFERRED EMBODIMENTS

The technical contents of the present invention will be described in detail in cooperation with drawings below.

The present invention proposes a high-magnesium concentrated liquid. In a first embodiment, the high-magnesium concentrated liquid comprises magnesium ranged from 60000-70000 ppm, sodium ranged from 1000-3200 ppm, potassium ranged from 300-3000 ppm, calcium ranged from 100-300 ppm, and the balance of water. In a second embodiment, the high-magnesium concentrated liquid comprises magnesium ranged from 40000-50000 ppm, sodium ranged from 8000-18000 ppm, potassium ranged from 8000-17000 ppm, calcium ranged from 15-250 ppm, and the balance of water.

Figure 1:
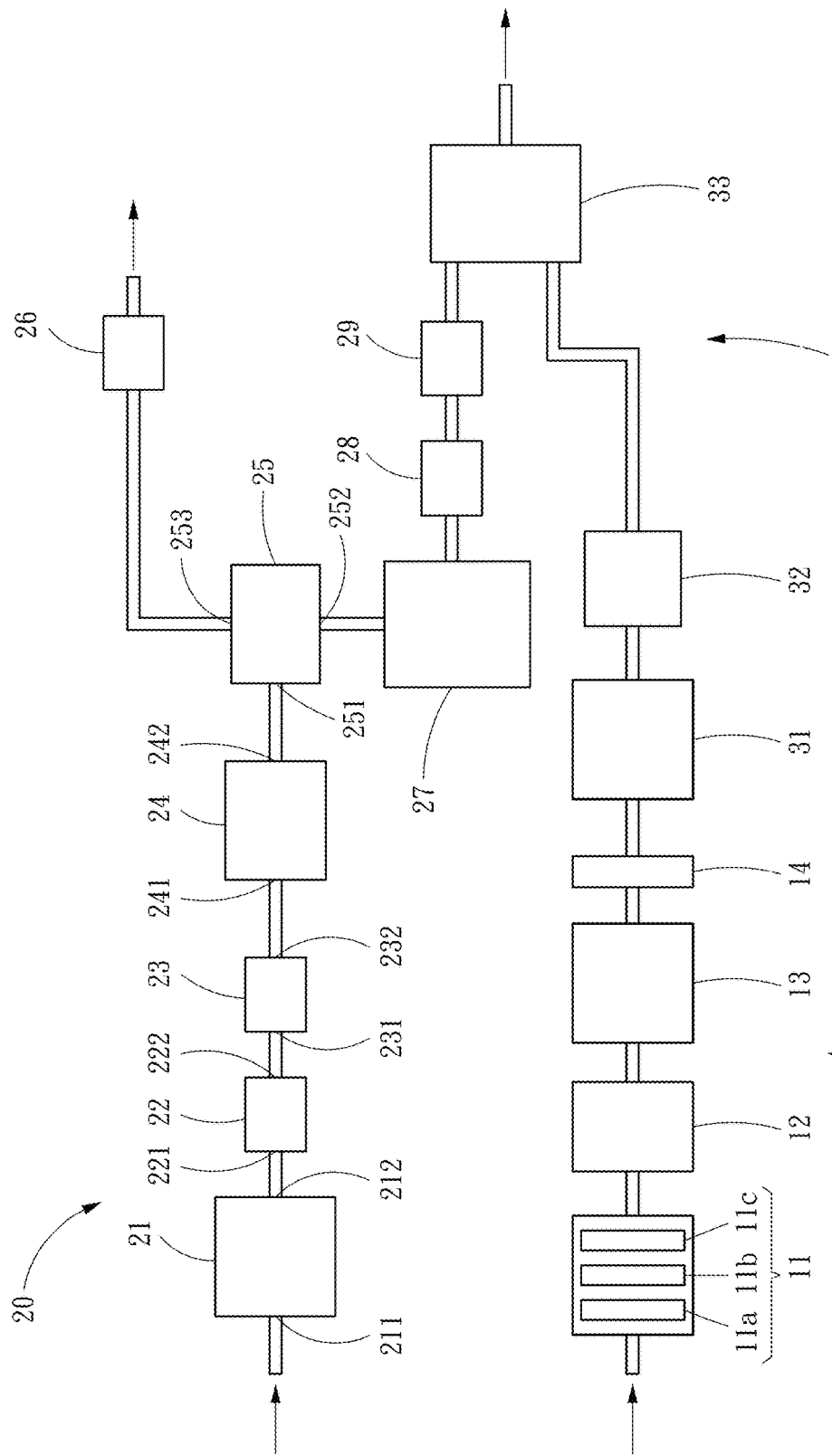
FIG. 1 is a diagram schematically showing a high-magnesium potable-water mixing system according to one embodiment of the present invention.
Figure 2A:
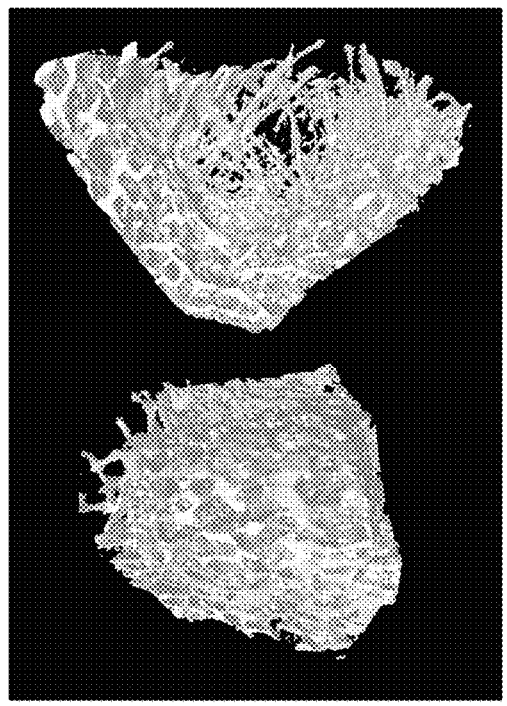
FIGS. 2A-2F are the Micro-CT-based bone density images of the rats of the experiment groups, control groups and comparison groups using a high-magnesium concentrated liquid according to a first embodiment of the present invention.
Figure 2B:
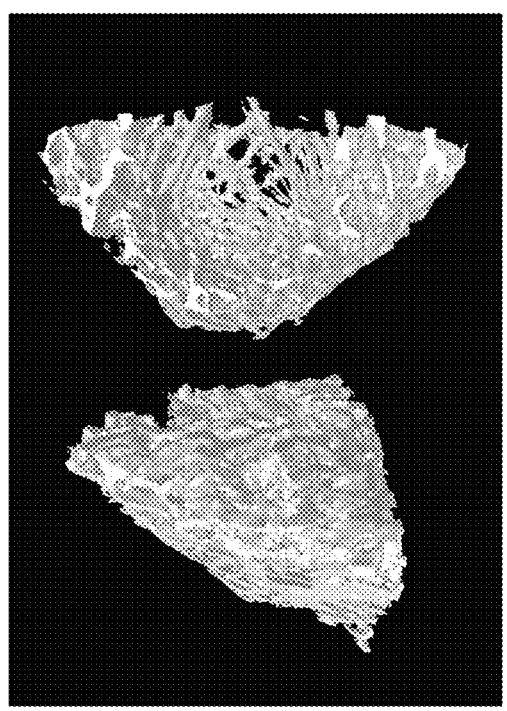
Figure 2C:
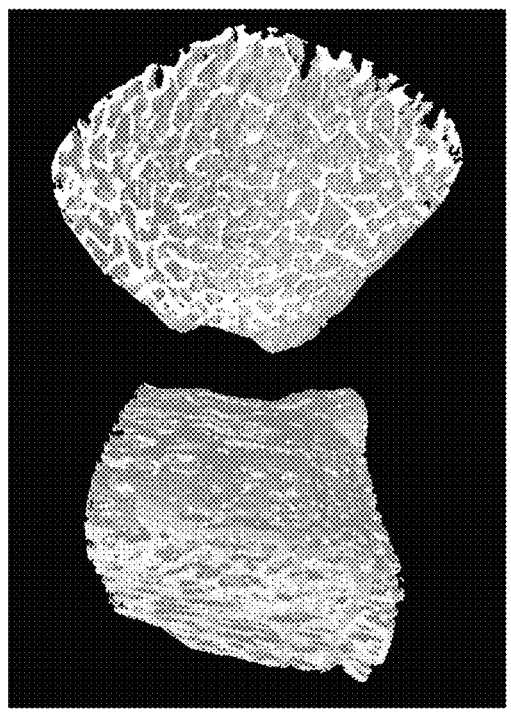
Figure 2D:
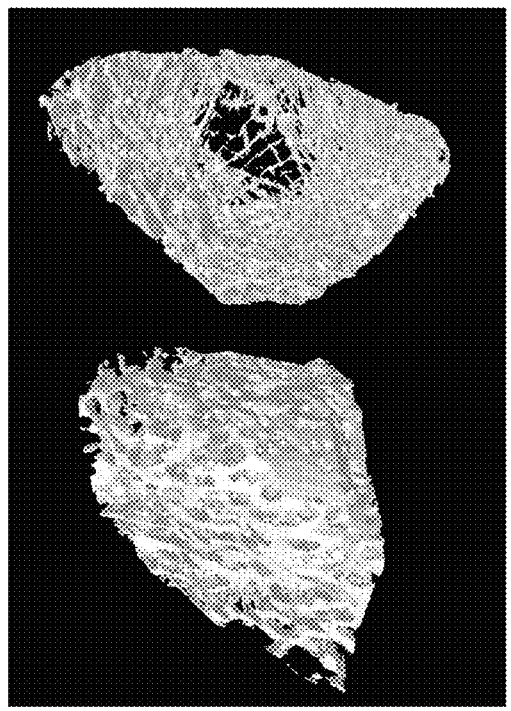
Figure 2F:
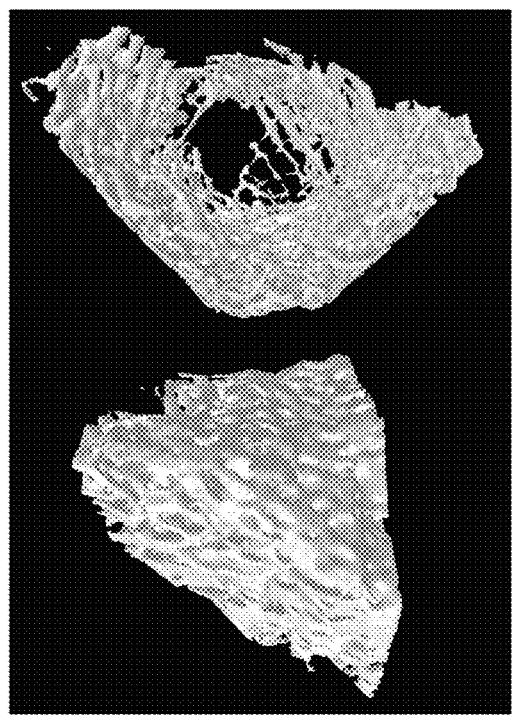
Figure 2E:
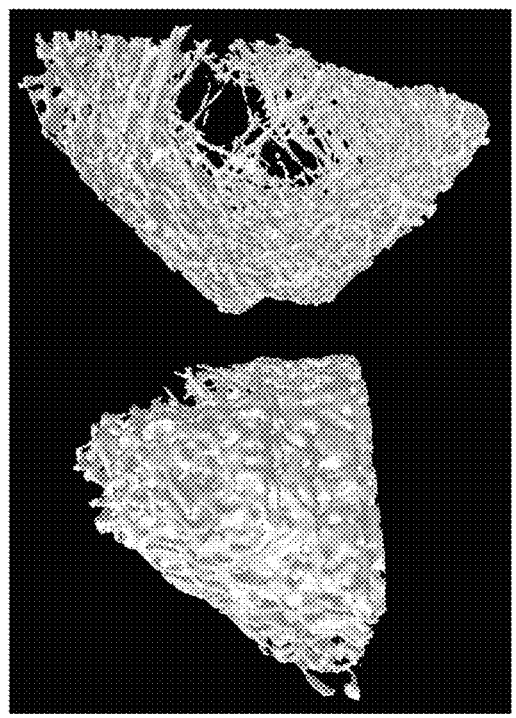
Figure 3B:
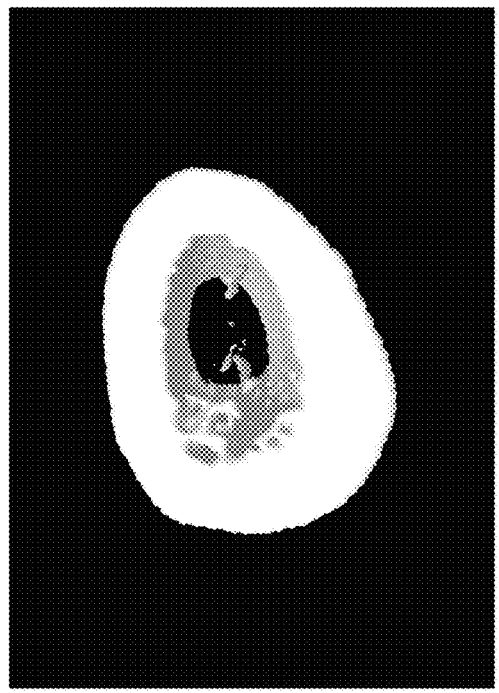
FIGS. 3A-3F are the Micro-CT-based trabecula images of the rats of the experiment groups, control groups and comparison groups using a high-magnesium concentrated liquid according to the first embodiment of the present invention.
Figure 3A:
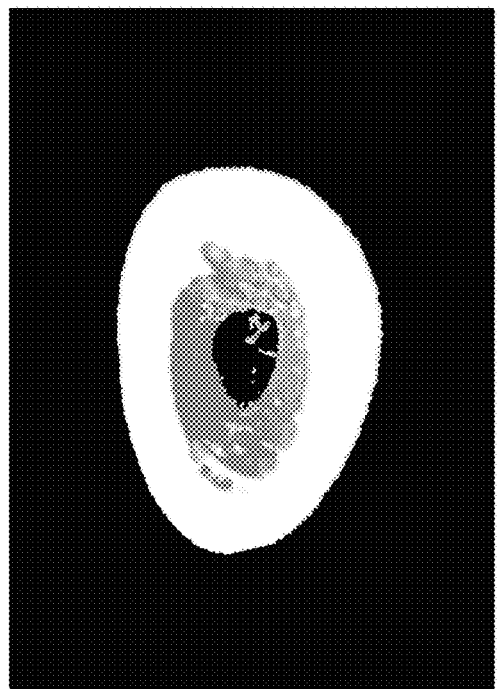
Figure 3D:
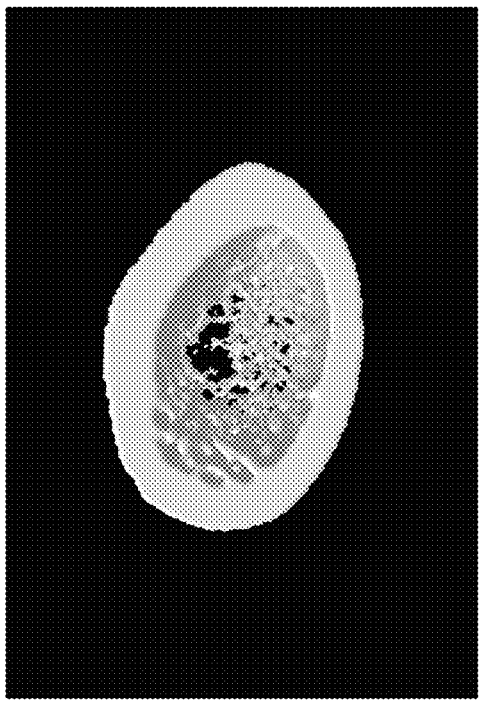
Figure 3C:
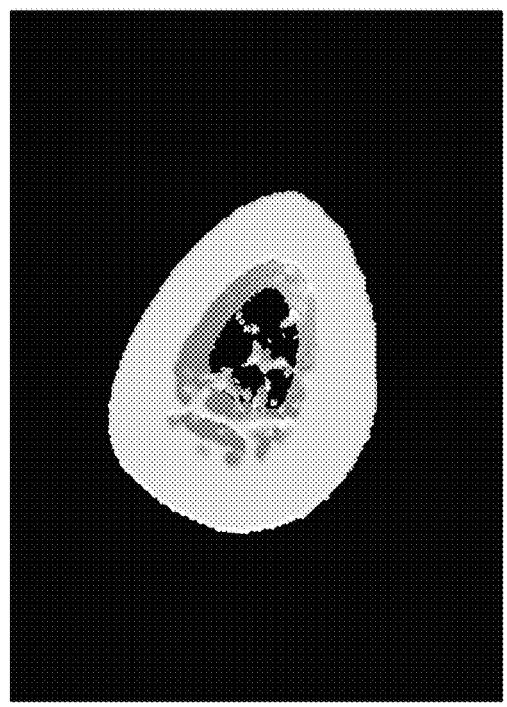
Figure 3F:
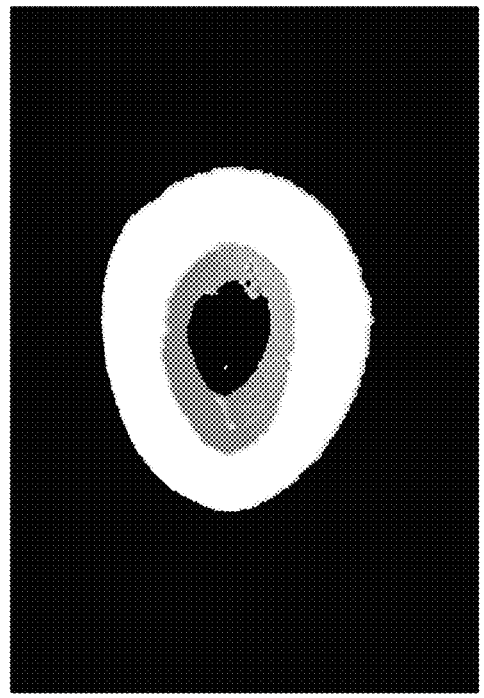
Figure 3E:
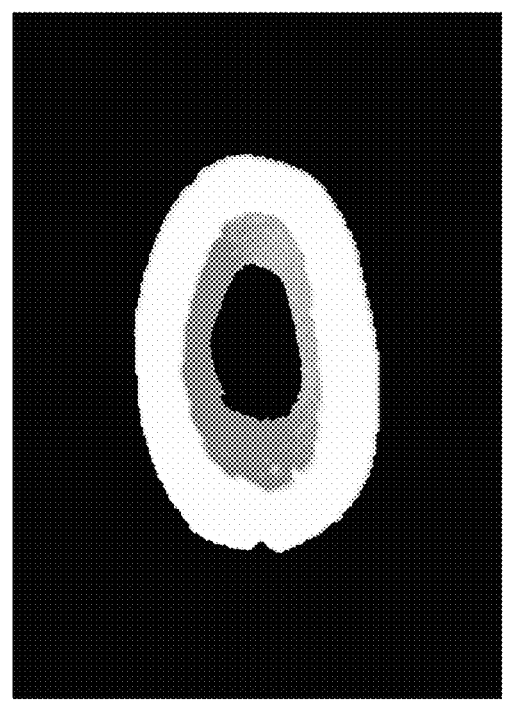

The present invention further proposes a high-magnesium potable-water mixing system. Refer to FIG. 1 a diagram schematically showing a high-magnesium potable-water mixing system according to one embodiment of the present invention. In this embodiment, the high-magnesium potable-water mixing system comprises a high-magnesium concentrated liquid output device 10, a purified water output device 20, and a liquid mixing device 30. The high-magnesium concentrated liquid output device 10 provides the above-mentioned high-magnesium concentrated liquid. The purified water output device 20 provides purified water. The liquid mixing device 30 interconnects with the high-magnesium concentrated liquid output device 10 and the purified water output device 20 and mixes the high-magnesium concentrated liquid and the purified water to generate a high-magnesium potable water.

In one embodiment, the high-magnesium concentrated liquid output device 10 is a device generating the high-magnesium concentrated liquid or a container storing the high-magnesium concentrated liquid. Refer to FIG. 1 for the high-magnesium concentrated liquid generation device. In the embodiment shown in FIG. 1, the high-magnesium concentrated liquid generation device comprises a filter 11, a vacuum low-temperature concentration unit 12, and an atmospheric evaporation unit 13. Based on the high-magnesium concentrated liquid generation device, the process for generating the high-magnesium concentrated liquid comprises Steps S1-S4.

In Step S1, providing deep ocean water and using the filter 11 to filter the deep ocean water to obtain a first concentrated liquid, which comprises magnesium ranged from 1900-3000 ppm, sodium ranged from 13000-21000 ppm, potassium ranged from 550-1000 ppm, calcium ranged from 600-1000 ppm, and the balance of water. In one embodiment, the deep ocean water comes from an ocean layer 200-1500 m deep, preferably 300-700 m deep. In the embodiment shown in FIG. 1, the filter 11 includes a microfiltration membrane 11a, an ultrafiltration membrane 11b, and a reverse osmosis membrane 11c. In one embodiment, the microfiltration membrane 11a has a first pore diameter of 0.025-10 μm, filtering out the suspended matters in the deep ocean water, such as soil, water bloom, microorganism, etc.; the ultrafiltration membrane 11b has a pore diameter of 5-10 nm, filtering out microparticles or bacteria in the deep ocean water; the reverse osmosis membrane 11c has a third pore diameter of 0.2-1.0 nm, filtering out salts in the deep ocean water.

In Step S2, using the vacuum low-temperature concentration unit 12 to concentrate the first concentrated liquid to obtain a second concentrated liquid, which comprises magnesium ranged from 10000-160000 ppm, sodium ranged from 60000-100000 ppm, potassium ranged from 3000-6000 ppm, calcium ranged from 300-500 ppm, and the balance of water. The vacuum low-temperature concentration unit 12 has a temperature of 50-70° C. and a pressure of 10-20 KPa.

In Step S3, using the atmospheric evaporation unit 13 to heat the second concentrated liquid to precipitate a crystalline salt, setting the second concentrated liquid still to let the crystalline salt settle down on the bottom, and then sucking the liquid on the top to acquire a third concentrated liquid. In one embodiment, the atmospheric evaporation unit 13 heats the second concentrated liquid at a temperature of 90-120° C.

In Step S4, cooling down the third concentrated liquid, and using a filter membrane 14 having a specified pore diameter to filter the third concentrated liquid and screen out impurities to acquire a high-magnesium concentrated liquid, wherein the filter membrane 14 has a pore diameter of 0.2-2.0 μm. After being filtered, the concentrations of the third concentrated liquid are unchanged. In other words, the concentrations of the third concentrated liquid are the same as the concentrations of the high-magnesium concentrated liquid. In the present invention, the high-magnesium concentrated liquid includes two compositions. In a first embodiment, the high-magnesium concentrated liquid comprises magnesium ranged from 60000-70000 ppm, sodium ranged from 1000-3200 ppm, potassium ranged from 300-3000 ppm, calcium ranged from 100-300 ppm, and the balance of water. In a second embodiment, the high-magnesium concentrated liquid comprises magnesium ranged from 40000-50000 ppm, sodium ranged from 8000-18000 ppm, potassium ranged from 8000-17000 ppm, calcium ranged from 15-250 ppm, and the balance of water.

The purified water output device 20 is a purification device filtering unpurified water to obtain purified water or a container storing purified water. In the embodiment shown in FIG. 1, the purified water output device 20 is a purification device and includes a first filter core 21, a low-pressure switch 22, a water intake electromagnetic valve 23, a booster pump 24, and a reverse osmosis core 25. The first filter core 21 includes a first inlet 211 and a first outlet 212. The low-pressure switch 22 includes a second inlet 221 connected with the first outlet 212 and a second outlet 222, detecting whether the unpurified water is persistently supplied to the first filter core 21. The water intake electromagnetic valve 23 includes a third inlet 231 connected with the second outlet 222 and a third outlet 232, controlling the flow rate of the unpurified water. The booster pump 24 includes a fourth inlet 241 connected with the third outlet 232 and a fourth outlet 242, pressurizing the unpurified water to increase the flow rate of the unpurified water. The reverse osmosis core 25 includes a fifth inlet 251 connected with the fourth outlet 242 and a fifth outlet 252.

The purified water output device 20 may further include a flush electromagnetic valve 26, a purified water storage tank 27, a heating element 28, and a sterilization element 29. The flush electromagnetic valve 26 is connected with a sixth outlet 253 of the reverse osmosis core 25, controlling the flow rate of the water flushing the reverse osmosis core 25. The purified water storage tank 27 is disposed between the reverse osmosis core 25 and the liquid mixing device 30, storing the purified water output by the fifth outlet 252. The heating element 28 is disposed between the reverse osmosis core 25 and the liquid mixing device 30, heating the purified water to generate hot water and supplying the hot water to the liquid mixing device 30. The sterilization element 29 is disposed between the reverse osmosis core 25 and the liquid mixing device 30, sterilizing the purified water to generate sterile water and supplying the sterile water to the liquid mixing device 30.

The liquid mixing device 30 includes a liquid storage tank 31, a suction pump 32, and a liquid mixing unit 33. The liquid storage tank 31 stores the high-magnesium concentrated liquid. The suction pump 32 sucks the high-magnesium concentrated liquid from the liquid storage tank 31. The liquid mixing unit 33 mixes the purified water output by the fifth outlet 252 and the high-magnesium concentrated water sucked from the liquid storage tank 31 to generate the high-magnesium potable water. The liquid mixing device 30 formulates the high-magnesium concentrated liquids into potable water having appropriate hardnesses for different applications.

The high-magnesium concentrated liquid of the first embodiment is used to improve osteoporosis. The high-magnesium concentrated liquid of the second embodiment is used to relieve fatigue. The experiment groups and comparison groups described thereinafter will be used to demonstrate the efficacies of the first embodiment and the second embodiment of the present invention.

With respect to the high-magnesium concentrated liquid of the first embodiment, the ovariectomized rats are used to simulate menopausal females. Owing to hormone variation, menopausal females lose their bones fast and suffer from osteoporosis easily. The rats used in the experiment groups, control group, and comparison groups are female Sprague-Dawley rats. The rats are fed with different proportions of the high-magnesium potable water beforehand. Then, the serum and tissue slices of the rats are analyzed.

The dosages of the high-magnesium concentrated liquid fed to the rats in experiment groups, control group and comparison groups are shown in Table.1. The unit of the dosage is milliliter or gram per kilogram of body weight. The control group is the group of unovariectomized rats. The supply of calcium citrate is to learn the influence of calcium on osteoporosis.

TABLE 1 the feeding conditions for experiment groups,
control group and comparison groups

| | High-Magnesium Concentrated Liquid (ml/kg) | Calcium Citrate (g/kg) |
|---|---|---|
| Experiment 1 (L) | 0.35 | 0 |
| Experiment 2 (H) | 1.4 | 0 |
| Experiment 3 (HC) | 1.4 | 0.5 |
| Control (N) | 0 | 0 |
| Comparison 1 (OVX) | 0 | 0 |
| Comparison 2 (OVXC) | 0 | 0.5 |

Table.2 shows the concentrations of alkaline phosphatase (ALP), glutamate oxaloacetate transaminase (GOT), blood urea nitrogen (BUN), creatinine (CRE), glutamic-pyruvic transaminase (GPT) in the serum of the rats fed with the test agents in the experiment groups, control group and comparison groups.

TABLE 2 the serum test results of the experiment groups,
control group and comparison groups

| | ALP (U/L) | BUN (mg/dL) | CRE (mg/dL) | GOT (U/L) | GPT (U/L) |
|---|---|---|---|---|---|
| Experiment 1 (L) | 100 | 25 | 0.88 | 90 | 60 |
| Experiment 2 (H) | 125 | 19 | 0.81 | 140 | 95 |
| Experiment 3 (HC) | 100 | 18 | 0.83 | 91 | 57 |
| Control (N) | 115 | 24.5 | 0.77 | 113 | 61 |
| Comparison 1 (OVX) | 202 | 21.5 | 0.83 | 101 | 60 |
| Comparison 2 (OVXC) | 130 | 17 | 0.85 | 75 | 75 |

Table.3 shows the concentrations of calcium, magnesium, potassium, sodium and phosphor in the serum of the rats fed with the test agents in the experiment groups, control group and comparison groups.

TABLE 3 the serum test results of the experiment groups,
control group and comparison groups

| | Calcium (mg/dL) | Magnesium (mmol/L) | Potassium (mmol/L) | Sodium (mmol/L) | Phosphor (mg/dL) |
|---|---|---|---|---|---|
| Experiment 1 (L) | 12.1 | 2.75 | 6.4 | 144 | 5.6 |
| Experiment 2 (H) | 12 | 3 | 6.25 | 144 | 7.9 |
| Experiment 3 (HC) | 12 | 2.8 | 6.5 | 144 | 6.8 |
| Control (N) | 12.7 | 3.35 | 6.9 | 140 | 9.7 |
| Comparison 1 (OVX) | 12.05 | 3.01 | 6.3 | 143 | 6.4 |
| Comparison 2 (OVXC) | 12.4 | 2.9 | 5.8 | 143 | 8 |

It is learned from Table.2: ALP of the ovariectomized rats rises from 115 (U/L) to 202 (U/L), which reflects osteoporosis. After the rats are fed with the high-magnesium concentrated liquid of the first embodiment, ALP is significantly lowered to 125 (U/L), which indicates that the high-magnesium concentrated liquid of the first embodiment can effectively improve osteoporosis. From the test results of BUN, CRE, GOT and GPT, it is learned: feeding the high-magnesium concentrated liquid does not affect the functions of livers and kidneys of the rats of the experiment groups. From Table.3, it is learned: feeding the high-magnesium concentrated liquid does not generate negative effects on the serum.

In addition to the serum examinations, the bone densities and the trabecula images of the rats of the experiment groups, control group and comparison groups are observed with a micro computed tomography (Micro-CT) technology, as shown in FIGS. 2A-2F and FIGS. 3A-3F. FIGS. 2A-2F are respectively the images of the bone densities of the rats of Experiment Group I, Experiment Group II, Experiment Group III, Control Group, Comparison Group I, and Comparison Group II. FIGS. 3A-3F are respectively the trabecula images of the rats of Experiment Group I, Experiment Group II, Experiment Group III, Control Group, Comparison Group I, and Comparison Group II. It can be observed in FIGS. 2A-2C: the rats of the experiment groups and the control group have higher bone density. It can be observed in FIG. 2E and FIG. 2F: the rats of the comparison groups have lower bone density. It can be observed in FIGS. 3A-3C: the rats of the experiment groups and the control group have more compact trabecula distribution. It can be observed in FIG. 3E and FIG. 3F: the rats of the comparison groups have less compact trabecula distribution.

Figure 4:
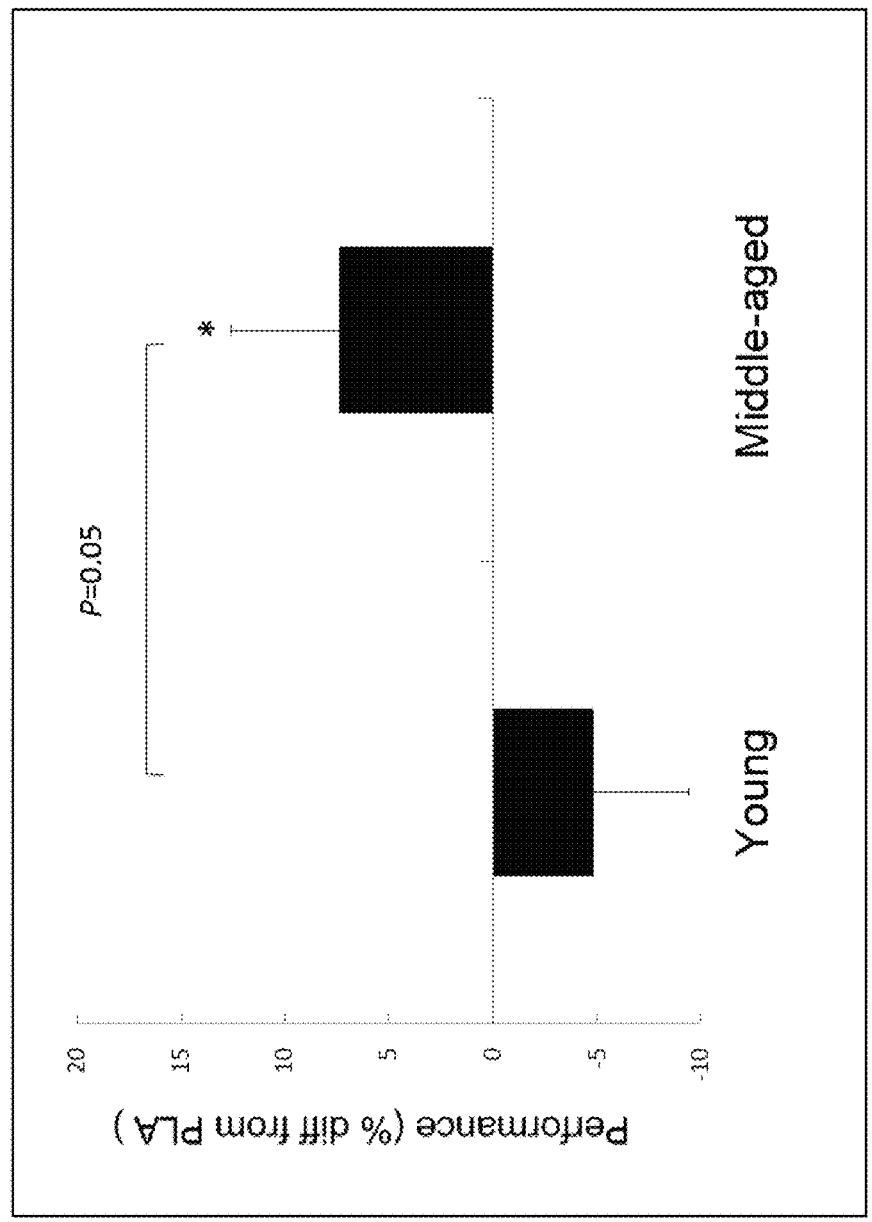
FIG. 4 is a diagram showing the exercise performance of the experiment group and the control group taking PLA and a high-magnesium concentrated liquid according to a second embodiment of the present invention.

With respect to the high-magnesium concentrated liquid of the second embodiment, middle-aged males are used in the experiment groups, and the young males are used in the control group. The exercise performance and numbers of red blood cells (RBCs) before, during and after exercise are measured, as shown in FIG. 4 and FIGS. 5A-5G. FIG. 4 shows the exercise performances of the experiment group and the control group, which take the high-magnesium concentrated liquid of the second embodiment and the placebo (PLA). The high-magnesium potable water taken by the experiment group is formulated to be potable water having a hardness of 600. It can be observed in FIG. 4: the exercise endurance performance of the control group taking the high-magnesium concentrated liquid does not improve but lowers by about 4.77%; the exercise endurance performance of the experiment group taking the high-magnesium concentrated liquid improves significantly and increases by about 7.36%.

Figure 5B:
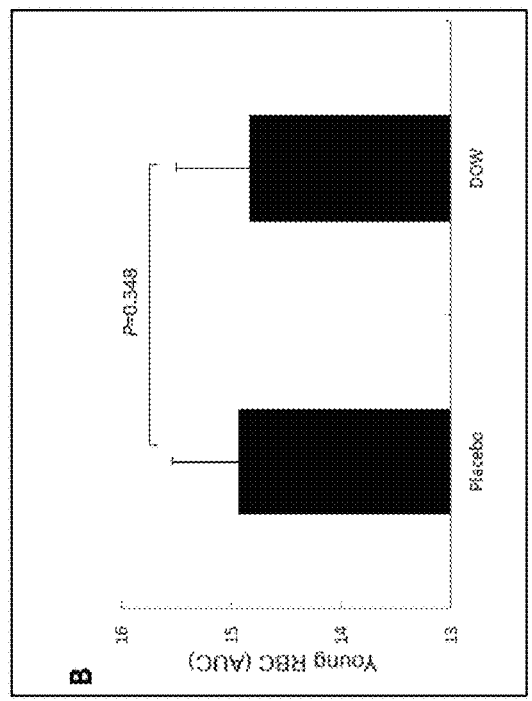
FIGS. 5A-5H are diagrams showing the variation of the number of RBCs and the value of tHB, which are measured before exercise, after exercise and two hours later after exercise, of the experiment group and the control group taking PLA and a high-magnesium concentrated liquid according to the second embodiment of the present invention.
Figure 5A:
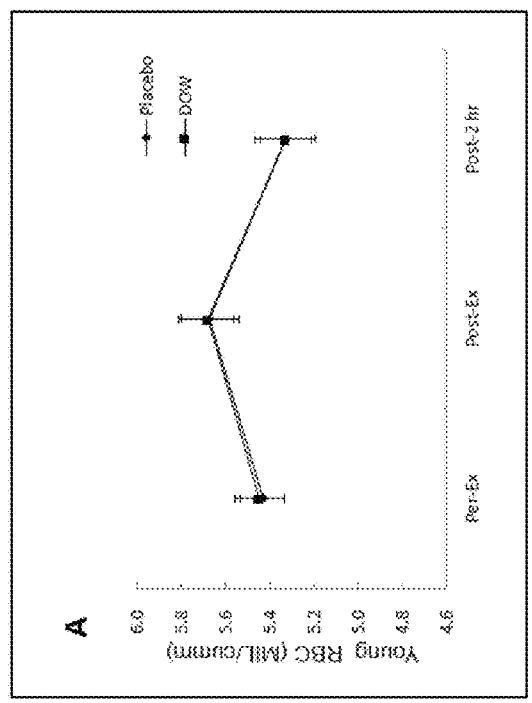
Figure 5D:
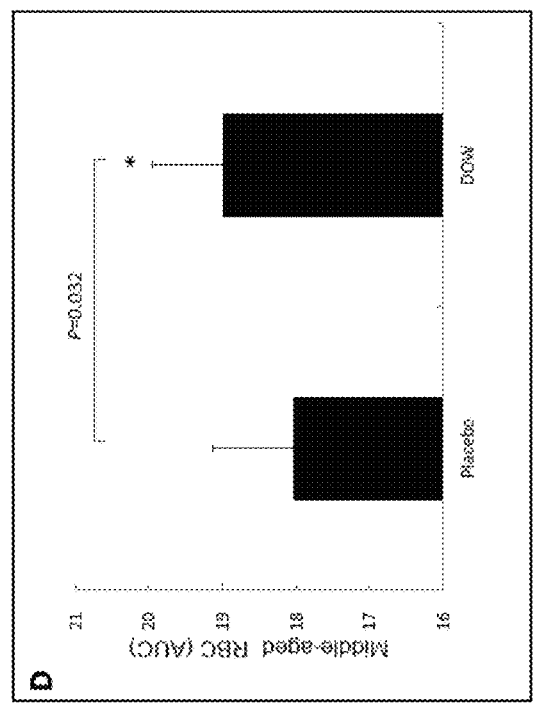
Figure 5C:
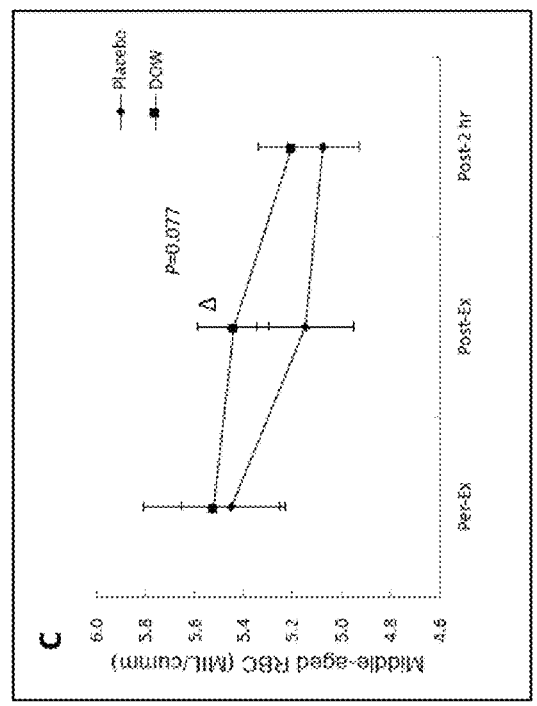
Figure 5E:
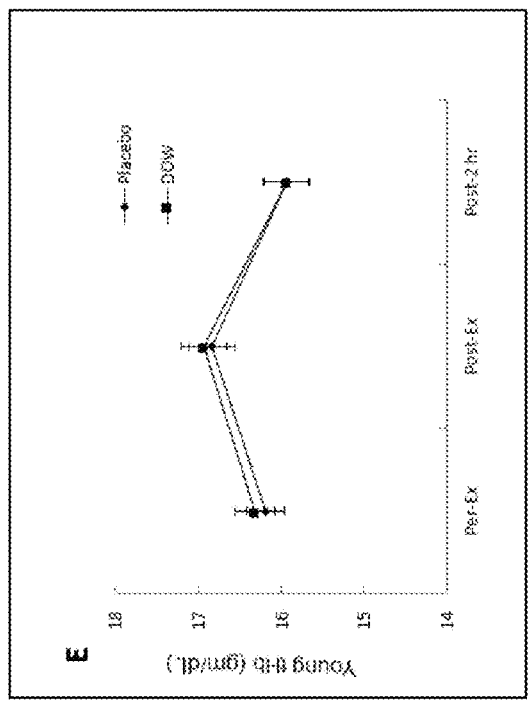
Figure 5F:
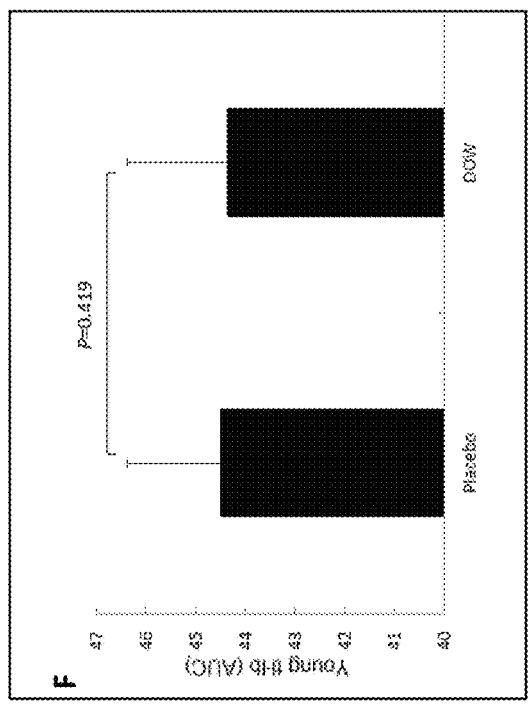
Figure 5H:
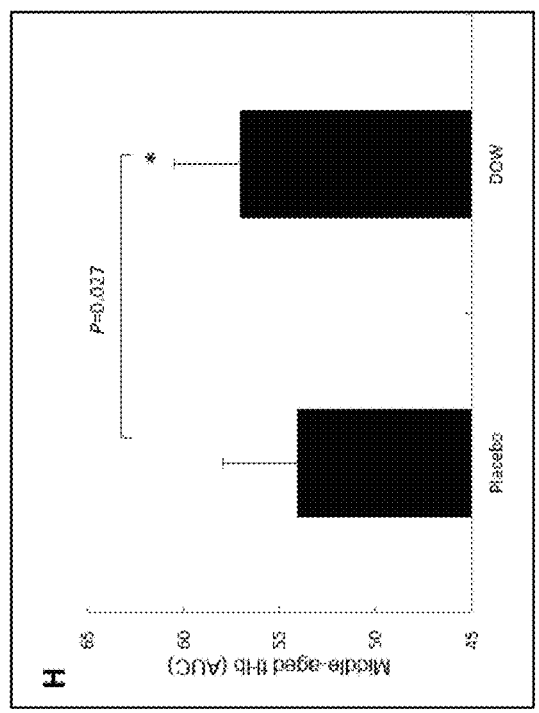
Figure 5G:
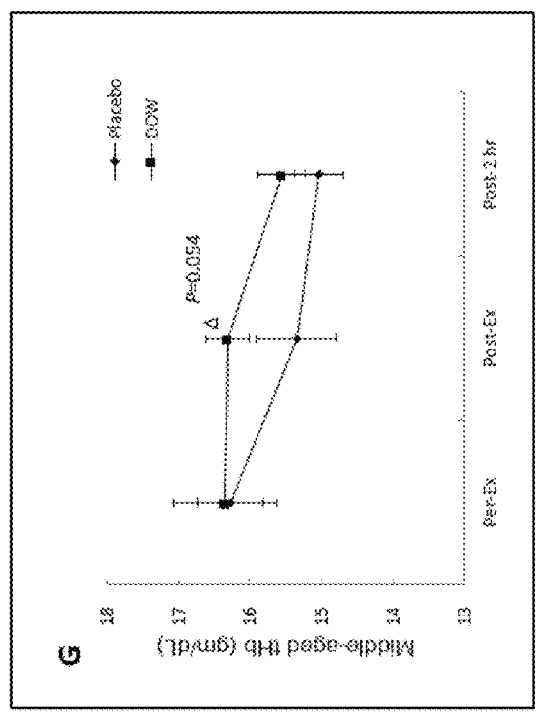

FIG. 5A and FIG. 5C shows the numbers of RBCs measured before exercise, after exercise, and two hours later after exercise for the experiment group and the control group, which take the high-magnesium concentrated liquid and PLA. FIG. 5B and FIG. 5D respectively show the areas under the curves of FIG. 5A and FIG. 5C. FIG. 5E and FIG. 5G shows the total hemoglobin (tHB) measured before exercise, after exercise, and two hours later after exercise for the experiment group and the control group, which take the high-magnesium concentrated liquid taking and PLA. FIG. 5F and FIG. 5H respectively show the areas under the curves of FIG. 5E and FIG. 5G. From the drawings, it can be observed: for the control group, taking the high-magnesium concentrated liquid and PLA does not influence RBCs and tHB; for the experiment group, taking the high-magnesium concentrated liquid significantly increases the number of RBCs and the value of tHB, however. The decrease of RBCs of the experiment group taking PLA may be attributed to hemolysis induced by exercise. Hemolysis impairs oxygen transportation, inhibits RBC-mediated vasorelaxation, and thus adversely affects the performance of exercise. The trend of tHB is similar to RBCs. Therefore, it is inferred: the high-magnesium concentrated liquid of the second embodiment can relieve the exercise-induced hemolysis and thus can enhance the exercise endurance of middle-aged males.

In conclusion, the compositions of the high-magnesium concentrated liquids of the present invention are experimentally proved to have the function of improve osteoporosis or relieve fatigue.

The present invention has been demonstrated in detail with the above embodiments. However, these embodiments are only to exemplify the present invention but not to limit the scope of the present invention. Any equivalent modification or variation according to the specification or claim of the present invention is to be also included within the scope of the present invention.

What is claimed is:

1. A production system for magnesium containing drinking-water, comprising:
   a magnesium concentrated liquid output device, including
      a filter filtering a deep ocean water to obtain a first concentrated liquid, a vacuum concentration unit connecting to the filter to concentrate the first concentrated liquid at 50° C.-70° C. to obtain a second concentrated liquid, an atmospheric evaporation unit connecting to the vacuum concentration unit to evaporate the second concentrated liquid to separate out a crystalline salt, and a filter membrane having a specified pore diameter connecting to the atmospheric evaporation unit; wherein the second concentrated liquid stands to let the crystalline salt be precipitated on the bottom of the second concentrated liquid and to let the liquid be drawn from the top of the second concentrated liquid to acquire a third concentrated liquid; and to let the third concentrated liquid be cooled, the filter membrane with a specified pore diameter filters the third concentrated liquid to output a magnesium concentrated liquid comprising magnesium ranged from 60000-70,000 ppm, sodium ranged from 1000-3,200 ppm, potassium ranged from 300-3,000 ppm, calcium ranged from 100-300 ppm, and a balance of water;
   a purified water output device comprising a reverse osmosis core, providing purified water;
   a liquid mixing device, connecting the magnesium concentrated liquid output device with the purified water output device, and the liquid mixing device mixing the magnesium concentrated liquid and the purified water to generate a magnesium drinking water;
   further comprising at least one of a heating element and a sterilization element disposed between the reverse osmosis core and the liquid mixing device.

2. The production system for magnesium containing drinking-water according to claim 1, wherein the liquid mixing device includes a liquid storage tank, a suction pump, and a liquid mixing unit, and the liquid storage tank stores the magnesium concentrated liquid; the suction pump draws the magnesium concentrated liquid from the liquid storage tank; and the liquid mixing unit mixes the purified water and the magnesium concentrated liquid drawn from the liquid storage tank to generate the magnesium drinking water.

3. The production system for magnesium containing drinking-water according to claim 1, wherein the purified water output device includes a first filter core, a low-pressure switch, a water intake electromagnetic valve, a booster pump, and the reverse osmosis core, wherein the first filter core includes a first inlet receiving unpurified water and a first outlet; the low-pressure switch includes a second inlet connected with the first outlet and a second outlet, detecting whether the unpurified water is supplied to the first filter core, and wherein the water intake electromagnetic valve includes a third inlet connected with the second outlet and a third outlet, controlling the flow rate of the unpurified water; the booster pump includes a fourth inlet connected with the third outlet and a fourth outlet, pressurizing the unpurified water to increase the flow rate of the unpurified water; and the reverse osmosis core includes a fifth inlet connected with the fourth outlet and a fifth outlet outputting purified water.

4. A production system for magnesium containing drinking-water, comprising:
   a magnesium concentrated liquid output device, including
      a filter filtering a deep ocean water to obtain a first concentrated liquid, a vacuum concentration unit connecting to the filter to concentrate the first concentrated liquid at 50° C.-70° C. to obtain a second concentrated liquid, an atmospheric evaporation unit connecting to the vacuum concentration unit to evaporate the second concentrated liquid to separate out a crystalline salt, and a filter membrane having a specified pore diameter connecting to the atmospheric evaporation unit; wherein the second concentrated liquid stands to let the crystalline salt be precipitated on the bottom of the second concentrated liquid and to let the liquid be drawn from the top of the second concentrated liquid to acquire a third concentrated liquid; and to let the third concentrated liquid be cooled, the filter membrane with a specified pore diameter filters the third concentrated liquid to output a magnesium concentrated liquid comprising magnesium ranged from 40000-50,000 ppm, sodium ranged from 8000-18,000 ppm, potassium ranged from 8000-17,000 ppm, calcium ranged from 15-250 ppm, and a balance of water;
   a purified water output device comprising a reverse osmosis core, providing purified water;
   a liquid mixing device, connecting the magnesium concentrated liquid output device with the purified water output device, and the liquid mixing device mixing the magnesium concentrated liquid and the purified water to generate a magnesium drinking water;

further comprising a heating element disposed between the reverse osmosis core and the liquid mixing device.

5. The production system for magnesium containing drinking-water according to claim 4, wherein the liquid mixing device includes a liquid storage tank, a suction pump, and a liquid mixing unit, and the liquid storage tank stores the magnesium concentrated liquid; the suction pump draws the magnesium concentrated liquid from the liquid storage tank; and the liquid mixing unit mixes the purified water and the magnesium concentrated liquid drawn from the liquid storage tank to generate the magnesium drinking water.

6. The production system for magnesium containing drinking-water according to claim 4, wherein the purified water output device includes a first filter core, a low-pressure switch, a water intake electromagnetic valve, a booster pump, and the reverse osmosis core, wherein the first filter core includes a first inlet receiving unpurified water and a first outlet; the low-pressure switch includes a second inlet connected with the first outlet and a second outlet, detecting whether the unpurified water is supplied to the first filter core; the water intake electromagnetic valve includes a third inlet connected with the second outlet and a third outlet, controlling the flow rate of the unpurified water; the booster pump includes a fourth inlet connected with the third outlet and a fourth outlet, pressurizing the unpurified water to increase the flow rate of the unpurified water; and the reverse osmosis core includes a fifth inlet connected with the fourth outlet and a fifth outlet outputting purified water.

7. A production system for magnesium containing drinking water comprising:
a magnesium concentrated liquid output device, including a filter filtering a deep ocean water to obtain a first concentrated liquid, a vacuum concentration unit connecting to the filter to concentrate the first concentrated liquid at $50^{degrees}$ C.-$70^{degrees}$ C. to obtain a second concentrated liquid, an atmospheric evaporation unit connecting to the vacuum concentration unit to evaporate the second concentrated liquid to separate out a crystalline salt, and a filter membrane having a specified pore diameter connecting to the atmospheric evaporation unit; wherein the second concentrated liquid stands to let the liquid be drawn from the top of the second concentrated liquid to acquire a third concentrated liquid; and wherein to let the third concentrated liquid be cooled, the filter membrane with a specified pore diameter filters the third concentrated liquid to output a magnesium concentrated liquid comprising magnesium ranged from 40,000 ppm-50,000 ppm, sodium ranged from 8,000-18,000 ppm, potassium ranged from 8,000 to 17,000 ppm, calcium ranged from 15-250 ppm, and a balance of water;
a purified water output device comprising a reverse osmosis core, providing purified water;
a liquid mixing device, connecting the magnesium concentrated liquid output device with the purified water output device, and the liquid mixing device mixing the magnesium concentrated liquid and the purified water to generate a magnesium drinking water;
and further comprising a sterilization element disposed between the reverse osmosis core and the liquid mixing device.

8. The production system for magnesium containing drinking water according to claim 7, wherein the liquid mixing device includes a liquid storage tank, a suction pump, and a liquid mixing unit, and the liquid storage tank stores the magnesium concentrated liquid; the suction pump draws the magnesium concentrated liquid from the liquid storage tank; and the liquid mixing tank mixes the purified water and the magnesium concentrated liquid drawn from the liquid storage tank to generate the drinking water.

9. The production system for magnesium containing drinking water according to claim 7, wherein the purified water output device includes a first filter core, a low-pressure switch, a water intake electromagnetic valve, a booster pump, and the reverse osmosis core, wherein the first filter core includes a first inlet receiving unpurified water and a first outlet; the low-pressure switch includes a second inlet connected with the first outlet and a second outlet, detecting whether the unpurified water is supplied to the first filter core, and wherein the water intake electromagnetic valve includes a third inlet connected with the second outlet and a third outlet, controlling the flow rate of the unpurified water; the booster pump includes a fourth inlet connected with the third outlet and a fourth outlet, pressurizing the unpurified water to increase the flow rate of the unpurified water; and the reverse osmosis core includes a fifth inlet connected with the fourth outlet and a fifth outlet outputting purified water.

10. The production system for magnesium containing drinking water according to claim 7, and additionally comprising a heating element disposed between the reverse osmosis core and the liquid mixing device.

* * * * *